US010905802B2

(12) United States Patent
Babcock

(10) Patent No.: US 10,905,802 B2
(45) Date of Patent: Feb. 2, 2021

(54) LUBRICIOUS MEDICAL DEVICE COATING WITH LOW PARTICULATES

(71) Applicant: Surmodics, Inc., Eden Prairie, MN (US)

(72) Inventor: David E. Babcock, Brooklyn Park, MN (US)

(73) Assignee: Surmodics, Inc., Eden Prairie, MN (US)

(*) Notice: Subject to any disclaimer, the term of this patent is extended or adjusted under 35 U.S.C. 154(b) by 0 days.

(21) Appl. No.: 15/643,564

(22) Filed: Jul. 7, 2017

(65) Prior Publication Data

US 2017/0304506 A1   Oct. 26, 2017

Related U.S. Application Data

(60) Continuation of application No. 15/165,650, filed on May 26, 2016, now Pat. No. 9,737,639, which is a division of application No. 13/745,397, filed on Jan. 18, 2013, now Pat. No. 9,375,517.

(60) Provisional application No. 61/587,944, filed on Jan. 18, 2012, provisional application No. 61/587,929, filed on Jan. 18, 2012.

(51) Int. Cl.
*A61L 29/08* (2006.01)
*A61L 31/10* (2006.01)
*A61L 27/34* (2006.01)
*A61L 29/14* (2006.01)

(52) U.S. Cl.
CPC ............ *A61L 29/085* (2013.01); *A61L 27/34* (2013.01); *A61L 29/14* (2013.01); *A61L 31/10* (2013.01); *A61L 2400/10* (2013.01); *A61L 2420/06* (2013.01); *A61L 2420/08* (2013.01)

(58) Field of Classification Search
CPC ........ C08L 39/06; A61L 27/34; A61L 29/085; A61L 31/10; A61L 2400/10; A61L 2420/06; A61L 2420/08; A61L 29/14
See application file for complete search history.

(56) References Cited

U.S. PATENT DOCUMENTS

| | | | |
|---|---|---|---|
| 4,195,637 A | 4/1980 | Gruntzig et al. |
| 4,973,493 A | 11/1990 | Guire |
| 4,979,959 A | 12/1990 | Guire |
| 4,990,357 A | 2/1991 | Karakelle et al. |
| 5,001,009 A | 3/1991 | Whitbourne et al. |
| 5,002,582 A | 3/1991 | Guire et al. |
| 5,039,485 A | 8/1991 | Conviser et al. |
| 5,041,089 A | 8/1991 | Mueller et al. |
| 5,087,246 A | 2/1992 | Smith |
| 5,263,992 A | 11/1993 | Guire |
| 5,318,587 A | 6/1994 | Davey |
| 5,382,234 A | 1/1995 | Cornelius et al. |
| 5,414,075 A | 5/1995 | Swan et al. |
| 5,512,329 A | 4/1996 | Guire et al. |
| 5,554,120 A | 9/1996 | Chen et al. |
| 5,571,089 A | 11/1996 | Crocker |
| 5,637,460 A | 6/1997 | Swan et al. |
| 5,662,960 A | 9/1997 | Hostettler et al. |
| 5,670,558 A | 9/1997 | Onishi et al. |
| 5,714,360 A | 2/1998 | Swan et al. |
| 5,731,087 A | 3/1998 | Fan et al. |
| 5,776,101 A | 7/1998 | Goy |
| 5,807,331 A | 9/1998 | Den Heijer et al. |
| 5,849,846 A | 12/1998 | Chen et al. |
| 5,858,653 A | 1/1999 | Duran et al. |
| 5,882,336 A | 3/1999 | Janacek |
| 5,891,109 A | 4/1999 | Inoue et al. |
| 6,066,118 A | 5/2000 | Inoue et al. |
| 6,077,698 A | 6/2000 | Swan et al. |
| 6,156,345 A | 12/2000 | Chudzik et al. |
| 6,176,849 B1 | 1/2001 | Yang et al. |
| 6,278,018 B1 | 8/2001 | Swan |
| 6,394,995 B1 | 5/2002 | Solar et al. |
| 6,517,515 B1 | 2/2003 | Eidenschink |
| 6,603,040 B1 | 8/2003 | Swan |
| 6,623,504 B2 | 9/2003 | Vrba et al. |
| 6,896,842 B1 | 5/2005 | Hamilton et al. |

(Continued)

FOREIGN PATENT DOCUMENTS

| | | |
|---|---|---|
| CN | 104185661 | 8/2016 |
| EP | 0747071 | 12/1996 |

(Continued)

OTHER PUBLICATIONS

"Communication Pursuant to Rules 161(1) and 162 EPC," for European Patent Application No. 13704280.0, dated Sep. 3, 2014 (2 pages).
"Communication Pursuant to Rules 161(1) and 162 EPC," for European Patent Application No. 15778502.3 dated May 29, 2017 (2 pages).
"Communication under Rule 71(3) EPC," for European Patent Application No. 13704280, dated Aug. 13, 2015 (7 pages).
"Extended European Search Report," for European Patent Application No. 15198514.0 dated Mar. 29, 2016 (6 pages).
"File History," for U.S. Appl. No. 13/745,397.

(Continued)

*Primary Examiner* — Anna R Falkowitz
(74) *Attorney, Agent, or Firm* — Pauly, DeVries Smith & Deffner LLC

(57) ABSTRACT

Embodiments of the invention include lubricious medical device coatings. In an embodiment the invention includes a coating for a medical device including a first layer comprising polyvinylpyrrolidone derivatized with a photoreactive group; and a first cross-linking agent comprising at least two photoreactive groups; a second layer disposed on the first layer comprising polyvinylpyrrolidone derivatized with a photoreactive group; a second cross-linking agent comprising at least two photoreactive groups; and a polymer comprising polyacrylamide, the polymer derivatized with at least one photoreactive group. Other embodiments are included herein.

20 Claims, 12 Drawing Sheets

(56) References Cited

U.S. PATENT DOCUMENTS

| | | | |
|---|---|---|---|
| 6,924,390 | B2 | 8/2005 | Swan |
| 7,056,533 | B2 | 6/2006 | Chudzik et al. |
| 7,138,541 | B2 | 11/2006 | Swan |
| 7,163,523 | B2 | 1/2007 | Devens, Jr. et al. |
| 7,192,484 | B2 | 3/2007 | Chappa et al. |
| 7,348,055 | B2 | 3/2008 | Chappa et al. |
| 7,550,444 | B2 | 6/2009 | Stucke et al. |
| 7,691,476 | B2 | 4/2010 | Finley et al. |
| 7,772,393 | B2 | 8/2010 | Guire et al. |
| 8,889,760 | B2 | 11/2014 | Kurdyumov et al. |
| 8,927,000 | B2 | 1/2015 | Chappa et al. |
| 9,340,876 | B2 | 5/2016 | Kim |
| 9,375,517 | B2 | 6/2016 | Babcock |
| 9,737,639 | B2 * | 8/2017 | Babcock ............... A61L 29/085 |
| 10,124,088 | B2 | 11/2018 | Chappa et al. |
| 10,342,898 | B2 | 7/2019 | Babcock |
| 2002/0002353 | A1 | 1/2002 | Michal et al. |
| 2003/0165613 | A1 | 9/2003 | Chappa et al. |
| 2005/0163853 | A1 | 7/2005 | Szente et al. |
| 2008/0213334 | A1 * | 9/2008 | Lockwood ............ A61L 31/145 424/423 |
| 2009/0263449 | A1 | 10/2009 | Mcgonigle et al. |
| 2010/0198168 | A1 | 8/2010 | Rooijmans |
| 2010/0272774 | A1 | 10/2010 | Chappa et al. |
| 2010/0274012 | A1 | 10/2010 | Guire et al. |
| 2011/0046255 | A1 | 2/2011 | Rooijmans |
| 2011/0059874 | A1 | 3/2011 | Rooijmans et al. |
| 2011/0144373 | A1 | 6/2011 | Swan et al. |
| 2011/0245367 | A1 | 10/2011 | Kurdyumov et al. |
| 2012/0046384 | A2 | 2/2012 | Kurdyumov et al. |
| 2012/0149934 | A1 | 6/2012 | Kurdyumov |
| 2012/0253296 | A1 | 10/2012 | Amano et al. |
| 2013/0143056 | A1 | 6/2013 | Swan et al. |
| 2013/0197433 | A1 | 8/2013 | Babcock |
| 2013/0337147 | A1 | 12/2013 | Chappa et al. |
| 2014/0004158 | A1 | 1/2014 | Mcgonigle |
| 2014/0162083 | A1 | 6/2014 | Kurdyumov et al. |
| 2014/0193474 | A1 * | 7/2014 | Babcock ............... A61L 29/041 424/422 |
| 2015/0140107 | A1 | 5/2015 | Slager et al. |
| 2016/0089480 | A1 | 3/2016 | Chappa et al. |
| 2016/0271300 | A1 | 9/2016 | Babcock |
| 2017/0182224 | A1 | 6/2017 | Babcock et al. |
| 2019/0330551 | A1 | 10/2019 | Babcock et al. |

FOREIGN PATENT DOCUMENTS

| | | | |
|---|---|---|---|
| EP | 0829264 | 3/1998 | |
| EP | 2505215 | 10/2012 | |
| EP | 2692365 | 2/2014 | |
| EP | 2804915 | 3/2016 | |
| EP | 3012301 | 4/2016 | |
| JP | 09276392 | 10/1997 | |
| JP | 11114052 | 4/1999 | |
| JP | 2001017536 | 1/2001 | |
| RU | 2627390 | 8/2017 | |
| WO | 03055611 | 7/2003 | |
| WO | 2006063181 | 6/2006 | |
| WO | WO 2008/104573 | * 9/2008 | ............ A61L 29/08 |
| WO | 2009091812 | 7/2009 | |
| WO | 2011123441 | 10/2011 | |
| WO | WO2011/123441 | * 10/2011 | ................ C07F 9/40 |
| WO | 2012003293 | 1/2012 | |
| WO | 2013109930 | 7/2013 | |
| WO | 2015029625 | 3/2015 | |
| WO | 2015075141 | 5/2015 | |
| WO | 2016053831 | 4/2016 | |
| WO | 2017116707 | 7/2017 | |

OTHER PUBLICATIONS

"File History," for U.S. Appl. No. 14/860,128.
"File History," for U.S. Appl. No. 15/165,650.
"First Office Action," for Chinese Patent Application No. 2013800057179, dated Oct. 9, 2015 (7 pages) with English translation.
"International Preliminary Report on Patentability," for PCT Application No. PCT/US2015/052565 dated Apr. 13, 2017 (10 pages).
"International Preliminary Report on Patentability," for PCT/US2013/022202, dated Jul. 31, 2014 (5 pages).
"International Search Report & Written Opinion," for PCT/US2015/052565 dated Dec. 9, 2015 (14 pages).
"International Search Report and Written Opinion," from PCT Application No. PCT/US2013/022202, dated Apr. 22, 2013 (9 pages).
"Office Action," for Japanese Patent Application No. 2014553466 dated Oct. 11, 2016 (5 pages) with English translation.
"Office Action," for Russian Patent Application No. 2014133462 dated Nov. 17, 2016 (7 pages) with English translation.
"Response to Communication Pursuant to Rules 161(1) and 162 EPC," for EP Patent Application No. 13704280.0, dated Sep. 3, 2014 and filed with the EPO Mar. 10, 2015 (19 pages).
"Response to Communication pursuant to Rules 70(2) and 70a(2) EPC," for European Patent Application No. 15198514.0 filed with the EPO Oct. 26, 2016 (2 pages).
"International Search Report and Written Opinion," for PCT Application No. PCT/US2016/066559 dated Sep. 6, 2017 (10 pages).
"Non-Final Office Action," for U.S. Appl. No. 14/860,128 dated Jan. 3, 2018 (15 pages).
"Office Action," for Japanese Patent Application No. 2017-057269 dated Jan. 9, 2018 (5 pages) with English summary.
"Office Action," for Mexican Patent Application No. MX/a/2014/008670 dated Sep. 3, 2017 (1 page), translation only.
"Response to Final Office Action," for U.S. Appl. No. 14/860,128, dated May 16, 2017 and filed with the USPTO Oct. 3, 2017 (8 pages).
"Response to Non-Final Office Action," for U.S. Appl. No. 14/860,128, dated Jan. 3, 2018 and filed with the USPTO Apr. 12, 2018 (7 pages).
"Communication Pursuant to Article 94(3) EPC," for European Patent Application No. 15778502.3 dated Oct. 19, 2018 (8 pages).
"International Preliminary Report on Patentability," for PCT Application No. PCT/US2016/066559 dated Jul. 12, 2018 (7 pages).
"Non-Final Office Action," for U.S. Appl. No. 15/375,442 dated Nov. 2, 2018 (21 pages).
"Notice of Allowance," for U.S. Appl. No. 14/860,128 dated Jul. 16, 2018 (11 pages).
"Notice of Allowance," for U.S. Appl. No. 15/375,442 dated Mar. 1, 2019 (8 pages).
"Office Action," for Canadian Patent Application No. 2,861,314 dated Jan. 15, 2019 (3 pages).
"Response to Communication Pursuant to Article 94(3) EPC," for European Patent Application No. 15778502.3 filed Feb. 5, 2019 (9 pages).
"Response to Communication Pursuant to Rules 161(1) and 162 EPC," for European Patent Application No. 16871770.0 filed Feb. 8, 2019 (84 pages).
"Response to Non Final Office Action," for U.S. Appl. No. 15/375,442, filed with the USPTO Jan. 24, 2019 (6 pages).
"Communication Pursuant to Article 94(3) EPC," for European Patent Application No. 15198514.0 dated May 10, 2019 (4 pages).
"Communication Pursuant to Article 94(3) EPC," for European Patent Application No. 15778502.3 dated Jun. 26, 2019 (6 pages).
"First Examination Report," for Indian Patent Application No. 6113/CHENP/2014 dated May 30, 2019 (4 pages).
"Office Action," for Canadian Patent Application No. 2,861,314 dated Jul. 16, 2019 (3 pages).
"Office Action," for Japanese Patent Application No. 2017-516919 dated Jun. 18, 2019 (16 pages) with English Translation.
"Preliminary Office Action," for Brazilian Patent Application No. 1120140176752 dated Aug. 20, 2019 (7 pages) with English Translation.
"Response to Communication pursuant to Article 94(3) EPC," dated May 10, 2019 (4 pages) for European Patent Application No. 15198514.0 filed with the EPO on Aug. 12, 2019, 2 pages.

(56) References Cited

OTHER PUBLICATIONS

"Response to Office Action," for Canadian Patent Application No. 2,861,314 filed with CIPO Apr. 18, 2019 (32 pages).
"Communication Pursuant to Article 94(3) EPC," for European Patent Application No. 16871770.0 dated Oct. 7, 2019 (5 pages).
"Office Action Response," for Canadian Patent Application No. 2,861,314 filed Jan. 13, 2020 (17 pages).
"Office Action," for Japanese Patent Application No. 2017-516919 dated Dec. 24, 2019 (12 pages) with English Translation.
"Office Action," for Japanese Patent Application No. 2018-174717 dated Oct. 1, 2019 (10 pages) with English Translation.
"Response to Communication Pursuant to Article 94(3) EPC," for European Patent Application No. 15778502.3 filed Oct. 24, 2019 (9 pages).
"Response to Communication Pursuant to Article 94(3) EPC," for European Patent Application No. 16871770.0 filed with the EPO Jan. 29, 2020 (11 pages).
"Response to Examination Report," for Indian Patent Application No. 6113/CHENP/2014 filed Feb. 14, 2020 (10 pages).
Shimizu, Hyoue et al., "Properties of Xylylene Diisocyanate and its Application for a Hardener of Paint," Journal of Network Polymer, Japan (2011) vol. 32, No. 6 pp. 310-316 (7 pages) with English Synopsis.

\* cited by examiner

LUBRICIOUS MEDICAL DEVICE COATING WITH LOW PARTICULATES

This application is a continuation of U.S. application Ser. No. 15/165,650, filed May 26, 2016, which is a divisional of U.S. application Ser. No. 13/745,397, filed Jan. 18, 2013, now U.S. Pat. No. 9,375,517, which claims the benefit of U.S. Provisional Application No. 61/587,929, filed Jan. 18, 2012 and U.S. Provisional Application No. 61/587,944, filed Jan. 18, 2012, the content of all of which is herein incorporated by reference in their entireties.

FIELD OF THE INVENTION

The present invention relates to coatings for medical devices. More specifically, the present invention relates to lubricious medical device coatings with low particulate generation and medical devices and methods relating to the same.

BACKGROUND OF THE INVENTION

Medical devices include, amongst others, those that are chronically implanted, devices that are transitorily implanted, and those that not implanted at all. Many types of medical device can be enhanced by reducing the friction between the device and the environment that surrounds the medical device, particularly during insertion of a device. A classic example of this is in the context of catheters that are inserted, at least transitorily, into the body of a subject. Reduction of friction can lead to enhanced patient comfort, procedural ease for the care provider, reduced chances for infection, as well as reduced tissue disruption, amongst other benefits. One approach to reducing the friction between a medical device and the environment surrounding the medical device is to apply a lubricious coating onto the medical device.

SUMMARY OF THE INVENTION

Embodiments of the invention include lubricious medical device coatings. In an embodiment the invention includes a coating for a medical device including a first layer that includes polyvinylpyrrolidone derivatized with a photoreactive group and a first cross-linking agent comprising at least two photoreactive groups The coating can also include a second layer disposed on the first layer comprising polyvinylpyrrolidone derivatized with a photoreactive group, a second cross-linking agent comprising at least two photoreactive groups, and a polymer comprising polyacrylamide, the polymer derivatized with at least one photoreactive group.

In an embodiment, the invention includes a medical device that has a substrate, a first layer disposed on the substrate, the first layer comprising polyvinylpyrrolidone derivatized with a photoreactive group, and a first cross-linking agent comprising at least two photoreactive groups. The medical device can also include a second layer disposed on the first layer comprising polyvinylpyrrolidone derivatized with a photoreactive group, a second cross-linking agent comprising at least two photoreactive groups, and a polymer comprising polyacrylamide, the polymer derivatized with at least one photoreactive group.

In an embodiment, the invention includes a method of making a medical device comprising applying a first coating solution onto a substrate to form a first layer, the first coating solution comprising polyvinylpyrrolidone derivatized with a photoreactive group, a first cross-linking agent comprising at least two photoreactive groups, and a first solvent. The method can also include applying a second coating solution onto the first layer to form a second layer, the second coating solution comprising polyvinylpyrrolidone derivatized with a photoreactive group, a second cross-linking agent comprising at least two photoreactive groups, a polymer comprising polyacrylamide, the polymer derivatized with at least one photoreactive group, and a second solvent.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As described above, one approach to reducing the friction between a medical device and the environment surrounding the medical device is to apply a lubricious coating onto the medical device. However, many lubricious coatings are relatively ineffective in reducing the friction between the device and the environment surrounding the device (such as an intravascular space, as one example). In addition, many lubricious coatings lack sufficient durability leading to a rapid increase in friction during the course of use. Finally, many lubricious coatings, after exposure to an aqueous environment (such as within a patient) release particulate matter that can be undesirable.

Figure 1:
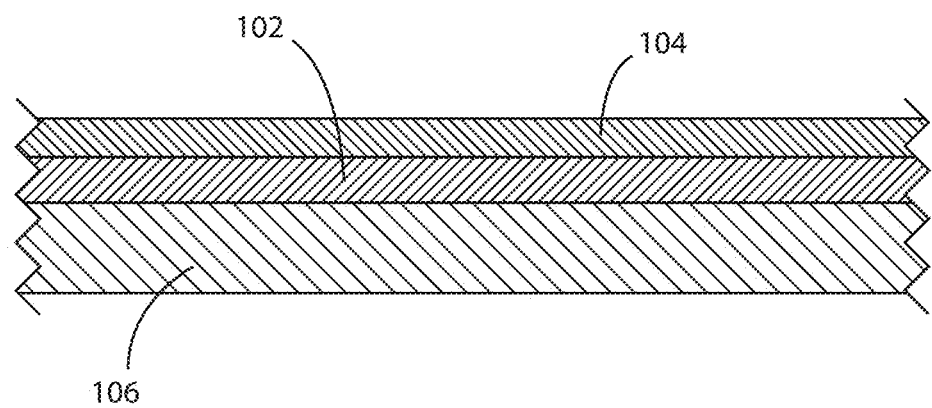
FIG. 1 is a schematic view of a coating in accordance with an embodiment herein.

Embodiments herein include coatings that are highly lubricious and relatively durable. In addition, embodiments herein include lubricious coatings that exhibit relatively low or reduced release of particulate matter. Referring now to FIG. 1, a schematic cross-sectional view is shown of a coating on a substrate in accordance with an embodiment herein. The coating can include a first layer 102 and a second layer 104. The second layer 104 can be disposed on the first layer 102. The first layer 102 can be disposed on a substrate 106. Exemplary substrate materials are described in greater detail below. In some embodiments, the first layer 102 is directly disposed on substrate 106. In other embodiments, other components may be disposed in between the first layer 102 and the substrate 106. The thickness of the first layer 102 and second layer 104, together, can be from about 100 nm to about 3000 nm when dry. In some embodiments, the thickness can be from about 1800 nm to about 2200 nm when dry. In some embodiments, the thickness can be about 2000 nm. In some embodiments, the thickness can be about 1000 nm. However, it will be appreciated that in some embodiments, the thickness can be from about 200 nm to about 400 nm. In some embodiments, the thickness can be about 300 nm.

In some embodiments, the first layer can include polyvinylpyrrolidone derivatized with a photoreactive group (or Photo-PVP) and a first cross-linking agent comprising at least two photoreactive groups. Methods for the preparation of photo-PVP are described in U.S. Pat. No. 5,414,075, incorporated herein by reference. Exemplary cross-linking agents comprising at least two photoreactive groups are described in greater detail below. Within the first layer, the components can be homogenously mixed in some embodiments.

In some embodiments, the ratio of polyvinylpyrrolidone derivatized with a photoreactive group in the first layer to the first cross-linking agent comprising at least two photoreactive groups is from about 2:1 to about 30:1 (wt./wt.). In some embodiments, the ratio of polyvinylpyrrolidone derivatized with a photoreactive group in the first layer to the first cross-linking agent comprising at least two photoreactive groups is from about 8:1 to about 20:1 (wt./wt.). In some embodiments, the ratio of polyvinylpyrrolidone derivatized with a photoreactive group in the first layer to the first cross-linking agent comprising at least two photoreactive groups is from about 8:1 to about 16:1 (wt./wt.). In some embodiments, the ratio of polyvinylpyrrolidone derivatized with a photoreactive group in the first layer to the first cross-linking agent comprising at least two photoreactive groups is about 13:1 (wt./wt.) In some embodiments, all components of the first layer are derivatized with photoreactive groups.

In some embodiments, the first layer can also include underivatized polyvinylpyrrolidone (PVP). The PVP can be of various molecular weights. In some embodiments, the ratio of polyvinylpyrrolidone derivatized with a photoreactive group in the first layer to non-derivatized polyvinylpyrrolidone in the first layer to the first cross-linking agent comprising at least two photoreactive groups is from about 13:0.1:1 to 13:8:1 (wt./wt./wt.). In some embodiments, the ratio of polyvinylpyrrolidone derivatized with a photoreactive group in the first layer to non-derivatized polyvinylpyrrolidone in the first layer to the first cross-linking agent comprising at least two photoreactive groups is about 13:5:1 (wt./wt./wt.). In some embodiments, the ratio of non-derivatized polyvinylpyrrolidone in the first layer to the first cross-linking agent comprising at least two photoreactive groups is from about 0.1:1 to 8:1 (wt./wt.).

In some embodiments, the second layer can include polyvinylpyrrolidone derivatized with a photoreactive group, a second cross-linking agent comprising at least two photoreactive groups, and a polymer comprising polyacrylamide, the polymer derivatized with at least one photoreactive group. The second cross-linking agent can be the same or different than the first cross-linking agent. In some embodiments, the polymer comprising polyacrylamide can also include acrylamido-2-methylpropanesulfonate groups (AMPS) and polyethyleneglycol segments. In a specific embodiment, the polymer comprising polyacrylamide can be N-Acetylated poly[acrylamide-co-sodium-2-acrylamido-2-methylpropanesulfonate-co-N-(3-(4-benzoylbenzamido) propyl)methacrylamide]-co-methoxy poly(ethylene glycol) monomethacrylate. Polymers comprising polyacrylamide in accordance with embodiments herein are described in U.S. Pat. Nos. 4,979,959; 5,263,992; and 5,512,329, the content of all of which is herein incorporated by reference in its entirety. In some embodiments, all components of the second layer are derivatized with photoreactive groups. Within the second layer, the components can be homogenously mixed in some embodiments.

In some embodiments PVP (underivatized PVP) can be added to the topcoat.

In some embodiments, the ratio of polyvinylpyrrolidone derivatized with a photoreactive group in the second layer to the polymer comprising polyacrylamide in the second layer is between approximately 10:1 and 1:10 (wt./wt.). In some embodiments, the ratio of polyvinylpyrrolidone derivatized with a photoreactive group in the second layer to the polymer comprising polyacrylamide in the second layer is between approximately 3:1 and 1:3 (wt./wt.). In some embodiments, the ratio of polyvinylpyrrolidone derivatized with a photoreactive group in the second layer to the polymer comprising polyacrylamide in the second layer is between approximately 2:1 and 1:2 (wt./wt.).

The coating can exhibit lubricity. It will be appreciated that lubricity can be observed as relative low friction. In some embodiments, the coating can be lubricious after exposure to water. The coating can exhibit lubricity of between 0 and 50 grams of force when wetted as measured by a vertical pinch test, such as that described below. The coating can exhibit lubricity of between 0 and 40 grams of force when wetted as measured by a vertical pinch test, such as that described below. In yet other embodiments the coating can exhibit lubricity of between 0 and 30 grams of force when wetted as measured by a vertical pinch test, such as that described below. In some embodiments the coating can exhibit lubricity of less than about 20 grams of force when wetted. In some embodiments the coating can exhibit lubricity of less than about 15 grams of force when wetted.

In various embodiments, the lubricity of the coating can be a durable property. For example, the lubricity can be retained over an extended period of time. For example, in some embodiments, lubricity can be maintained over a plurality of frictional testing cycles. In some embodiments, the coating can exhibit a lubricity of between 0 and 30 grams of force when wetted for at least 10 consecutive testing cycles. In some embodiments, such as where at least 15 frictional test cycles are performed, the measured lubricity will increase no more than 30% between the average of cycles 1-5 and the average of cycles 10-15 of the testing.

The coating can exhibit a relatively low amount of particulate release when exposed to an aqueous environment. For example, the coating will generate less than 70,000 particles of greater than 10 microns in size in an aqueous environment. In some embodiments, the coating will generate less than 50,000 particles of greater than 10 microns in size in an aqueous environment. In some embodiments, the coating will generate less than 30,000 particles of greater than 10 microns in size in an aqueous environment. In some embodiments, the coating will generate less than 25,000 particles of greater than 10 microns in size in an aqueous environment. In some embodiments, the coating will generate less than 20,000 particles of greater than 10 microns in size in an aqueous environment. In some embodiments, the coating will generate less than 15,000 particles of greater than 10 microns in size in an aqueous environment. In some embodiments, the coating will generate less than 10,000 particles of greater than 10 microns in size in an aqueous environment. In some embodiments, the coating will generate less than 8,000 particles of greater than 10 microns in size in an aqueous environment. In some embodiments, the coating will generate less than 6,000 particles of greater than 10 microns in size in an aqueous environment. It will be appreciated that in accordance with various embodiments herein, the properties of lubricity and low particulate release are both present.

Photoreactive Groups

As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Unless otherwise stated, references to photoreactive groups herein shall also include the reaction products of the photoreactive groups. Photoreactive groups respond to specific applied external stimuli to undergo active specie generation with resultant covalent bonding to an adjacent chemical structure. For example, in an embodiment, a photoreactive group can be activated and can abstract a hydrogen atom from an alkyl group. A covalent bond can then form between the compound with the photoreactive group and the compound with the C—H bond. Suitable photoreactive groups are described in U.S. Pat. No. 5,002,582, the disclosure of which is incorporated herein by reference.

Photoreactive groups can be chosen to be responsive to various portions of actinic radiation. Typically, groups are chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

In some embodiments, the photoreactive group is an aryl ketone, such as acetophenone, benzophenone, anthrone, and anthrone-like heterocycles (i. e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinone such as, for example anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate.

Other photoreactive groups include the diazirines (—$CHN_2$) such as 3-trifluoromethyl-3-phenyldiazirine; and ketenes (—CH=C=O) such as ketene and diphenylketene.

In particular embodiments, the photoreactive groups are aryl ketones, such as benzophenone.

Cross-Linking Agents

Cross-linking agents used in accordance with embodiments herein can include those with at least two photoreactive groups. Exemplary cross-linking agents are described in U.S. Publ. Pat. App. No. 2011/0245367, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second cross-linking agents comprising a linking agent having formula Photo$^1$-LG-Photo$^2$, wherein Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second cross-linking agents comprising a linking agent having a formula selected from:

(a)

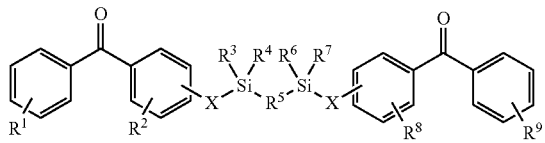

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)

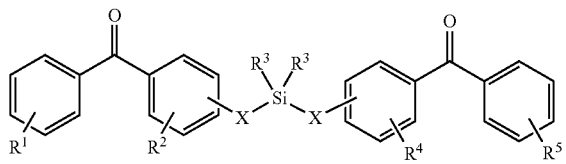

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)

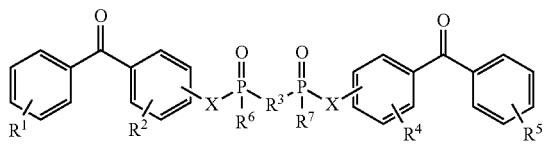

wherein R1, R2, R4 and R5 are any substitution; R3 is any substitution; R6 and R7 are alkyl, aryl, or a combination thereof; and each X can independently be O, N. Se, S, alkylene, or a combination thereof; and (d)

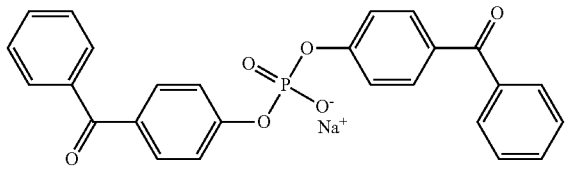

In a particular embodiment, the cross-linking agent can be bis(4-benzoylphenyl) phosphate.

In some embodiments, the photoactivatable cross-linking agent can be ionic, and can have good solubility in an aqueous composition, such as the first and/or second coating composition. Thus, in some embodiments, at least one ionic photoactivatable cross-linking agent is used to form the coating. In some cases, an ionic photoactivatable cross-linking agent can crosslink the polymers within the second coating layer which can also improve the durability of the coating.

Any suitable ionic photoactivatable cross-linking agent can be used. In some embodiments, the ionic photoactivatable cross-linking agent is a compound of formula I: $X_1$—Y—$X_2$ where Y is a radical containing at least one acidic group, basic group, or a salt of an acidic group or basic group. $X_1$ and $X_2$ are each independently a radical containing a latent photoreactive group. The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable cross-linking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable cross-linking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable cross-linking agent can be a compound having the formula:

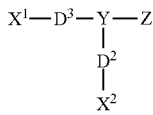

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Additional exemplary degradable ionic photoactivatable cross-linking agents are described in US Patent Application Publication US 2011/0144373 (Swan et al., "Water Soluble Degradable Crosslinker"), the disclosure of which is incorporated herein by reference.

In some aspects a non-ionic photoactivatable cross-linking agent can be used. In one embodiment, the non-ionic photoactivatable cross-linking agent has the formula $XR_1R_2R_3R_4$, where X is a chemical backbone, and $R_1$, $R_2$, $R_3$, and $R_4$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable cross-linking agent can be represented by the formula:

$PG^2$-$LE^2$-X-$LE^1$-$PG^1$ wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic cross-linking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable cross-linking agents can include, for example, those described in U.S. Provisional Application 61/494,724 filed Jun. 8, 2011 (now U.S. application Ser. No. 13/490,994) (Swan et al., "Photo-Vinyl Primers/Crosslinkers"), the disclosure of which is incorporated herein by reference. Exemplary cross-linking agents can include non-ionic photoactivatable cross-linking agents having the general formula $R^1$—X—$R^2$, wherein $R^1$ is a radical comprising a vinyl group, X is a radical comprising from about one to about twenty carbon atoms, and $R^2$ is a radical comprising a photoreactive group.

Some suitable cross-linking agents are those formed by a mixture of the chemical backbone molecule (such as pentaerythritol) and an excess of a derivative of the photoreactive group (such as 4-bromomethylbenzophenone). An exemplary product is tetrakis(4-benzoylbenzyl ether) of pentaerythritol (tetrakis(4-benzoylphenylmethoxymethyl) methane). See U.S. Pat. Nos. 5,414,075 and 5,637,460.

A single photoactivatable cross-linking agent or any combination of photoactivatable cross-linking agents can be used in forming the coating. In some embodiments, at least one nonionic cross-linking agent such as tetrakis(4-benzoylbenzyl ether) of pentaerythritol can be used with at least one ionic cross-linking agent. For example, at least one non-ionic photoactivatable cross-linking agent can be used with at least one cationic photoactivatable cross-linking agent such as an ethylenebis(4-benzoylbenzyldimethylammonium) salt or at least one anionic photoactivatable cross-linking agent such as 4,5-bis(4-benzoyl-phenylmethyleneoxy)benzene-1,3-disulfonic acid or salt. In another example, at least one nonionic cross-linking agent can be used with at least one cationic cross-linking agent and at least one anionic cross-linking agent. In yet another example, a least one cationic cross-linking agent can be used with at least one anionic cross-linking agent but without a non-ionic cross-linking agent.

An exemplary cross-linking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

A further exemplary cross-linking agent is ethylenebis (4-benzoylbenzyldimethylammonium) dibromide. This agent can be prepared as described in U.S. Pat. No. 5,714,360, the content of which is herein incorporated by reference.

Further cross-linking agents can include the cross-linking agents described in U.S. Publ. Pat. App. No. 2010/0274012 and U.S. Pat. No. 7,772,393 the content of all of which is herein incorporated by reference.

In some embodiments, cross-linking agents can include boron-containing linking agents including, but not limited to, the boron-containing linking agents disclosed in U.S. 61/666,516, entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

(I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

Additional agents for use with embodiments herein can include stilbene-based reactive compounds including, but not limited to, those disclosed in U.S. 61/736,436, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, cross-linking agents, hydrophilic coatings, and associated reagents are disclosed in US2011/0059874; US 2011/0046255; and US 2010/0198168, the content of all of which is herein incorporated by reference.

Methods of Forming the Coating

In some embodiments, a first coating solution is formed by combining compounds with a solvent. For example, the compounds can include comprising polyvinylpyrrolidone derivatized with a photoreactive group and a first cross-linking agent comprising at least two photoreactive groups. In some embodiments, the first coating solution can also include non-derivatized polyvinylpyrrolidone. The solvent for the first coating solution can include various components. In some embodiments, the solvent for the first coating solution can be 100% IPA. In some embodiments, the solvent for the first coating solution can include water and isopropyl alcohol (IPA). The proportion of IPA to water can be between about 95% IPA-5% water to about 10% IPA-90% water. For example in some embodiments, the ratio of IPA:water can be about 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, or can be within a range with endpoints including any two of those ratios such that the total relative portions of IPA and water are equal to 100. In some embodiments, the solvent can include about 75% isopropyl alcohol and about 25% water.

In some embodiments of the present disclosure other exemplary polar solvents (e.g. acetone, alcohols and DMSO) may be substituted for those described above.

In some embodiments, a second coating solution is formed by combining compounds with a solvent. For example, the compounds can include polyvinylpyrrolidone derivatized with a photoreactive group, a second cross-linking agent comprising at least two photoreactive groups, and a polymer comprising polyacrylamide, the polymer derivatized with at least one photoreactive group. The solvent for the second coating solution can include various components. In some embodiments, the solvent for the second coating solution can include water and isopropyl alcohol (IPA). The proportion of IPA to water can be from about 0% IPA-100 water to about 60 IPA-40 water. For example in some embodiments, the ratio of IPA:water can be about 0:100, 5:95, 10:90, 15:85, 20:80, 25:75, 30:70, 35:65, 40:60, 45:55, 50:50, 55:45, 60:40, or can be within a range with endpoints including any two of those ratios such that the total relative portions of IPA and water are equal to 100. In some embodiments, the solvent can include about 15% isopropyl alcohol and about 85% water.

The viscosity of the solutions can vary. In some embodiments, the viscosity of the second solution is less than about 100 centipoise (cP). In some embodiments, the viscosity of the second solution is equal to or less than about 90, 80, 70 60, 50, 40, 30, 20, or 10 cP.

The first coating solution can be applied to a substrate. Prior to application of the coating solution to the substrate, many different pretreatment steps can be taken. In some embodiments, the surface of the substrate can be cleaned. For example, the surface can be wiped or dipped into an alcohol such as isopropyl alcohol. In some embodiments, the substrate can be put into a detergent solution such as a VALTRON solution and sonicated. In some embodiments, a compound can be disposed on the surface of the substrate to act as a tie layer. In some embodiments the surface of the substrate can be sterilized.

Many different techniques can be used to apply the solution to the substrate. By way of example, exemplary techniques can include drop coating, blade coating, dip coating, spray coating, and the like. In various embodiments, the solution is applied by dip coating. The speed of dip coating can vary. For example, the substrate can be dipped into the first coating solution and then withdrawn at speeds between 0.01 and 10 cm/s. In some embodiments, the substrate can be dipped into the first coating solution and then withdrawn at speeds between 0.1 and 4 cm/s. In some embodiments, the substrate can be dipped into the first coating solution and then withdrawn at speeds between 0.1 and 0.5 cm/s. In some embodiments, the substrate can be withdrawn at speeds between 0.2 and 0.4 cm/s. In some embodiments, the substrate can be withdrawn at speeds of about 0.3 cm/s.

After the first coating solution is applied to the substrate, then actinic radiation, such as UV radiation, can be applied to activate photoreactive groups within the components of the first coating solution forming the first layer. Actinic radiation can be provided by any suitable light source that promotes activation of the photoreactive groups. Preferred light sources (such as those available from Dymax Corp.) provide UV irradiation in the range of 190 nm to 360 nm. An exemplary UV light source is a Dymax 2000-EC series UV flood lamp with a 400 Watt metal halide bulb. A suitable dose of radiation is in the range of from about 0.5 mW/cm$^2$ to about 2.0 mW/cm$^2$. Optionally, the first coating solution can be dried, before or during application of the actinic radiation.

The second coating solution can be applied on top of the first coating layer. Many different techniques can be used to apply the solution to the substrate. In a particular embodiment, the solution is applied by dip coating. The speed of dip coating can vary. For example, the substrate can be dipped into the second coating solution and then withdrawn at speeds between 0.01 and 10 cm/s. In some embodiments, the substrate can be dipped into the second coating solution and then withdrawn at speeds between 0.1 and 4 cm/s. In some embodiments, the substrate can be dipped into the second coating solution and then withdrawn at speeds between 0.1 and 0.5 cm/s. In some embodiments, the substrate can be withdrawn at speeds between 0.2 and 0.4 cm/s. In some embodiments, the substrate can be withdrawn at speeds of about 0.3 cm/s.

After the second coating solution is applied, then actinic radiation, such as UV radiation at a desirable wavelength, can be applied to activate photoreactive groups within the components of the second coating solution. Optionally, the second coating solution can be dried, before or during application of the actinic radiation.

Substrates

Substrates can be partially or entirely fabricated from a metal, ceramic, glass, or the like, or a combination thereof. Substrates can include polymers such as polyurethanes and polyurethane copolymers, polyethylene, polyolefins, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single material, or a combination of materials.

Substrate polymers can also include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

In some embodiments, the substrate includes a polymer selected from the group consisting of polyamide, polyimide, polyether block amide (PEBAX), polyether ether ketone (PEEK), high density polyethylene (HDPE), polyethylene, polyurethane, and polyethylene vinyl acetate.

Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

Medical Devices

The methods and materials of the invention can be utilized to coat virtually any medical device for which it is desired to provide a hydrophilic and lubricious coating on a surface thereof. In particular, the coatings are particularly useful for medical articles that can be inserted into and moved within the body.

Exemplary medical devices include vascular implants and grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; interventional cardiology devices including guide wires and leads (e.g. pacing, delivering electricity, defibrillation); anastomosis devices and anastomotic closures; aneurysm exclusion devices; biosensors, such as glucose sensors; cardiac sensors (and other sensors for analytical purposes); birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff; sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

Figure 2:
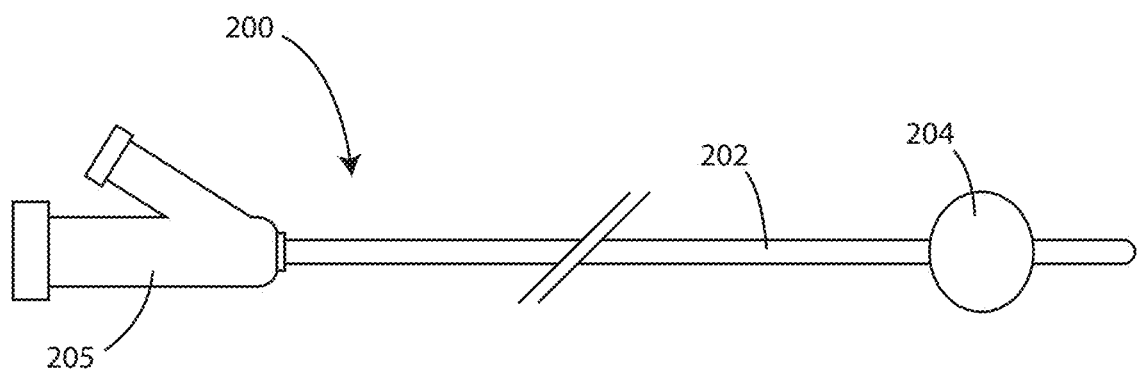
FIG. 2 is a schematic view of a device in accordance with an embodiment herein.

Referring now to FIG. 2, a schematic view of an exemplary device is shown in accordance with a specific embodiment. The device 200 can be, for example, a catheter, such as an angioplasty balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Further examples of exemplary devices are described in greater detail below. The device 200 includes a catheter shaft 202 and a manifold end 205. The device 200 also includes an inflatable balloon 204 disposed around the catheter shaft 202. In FIG. 2, the balloon 204 is shown in an inflated configuration. The catheter shaft 202 can include a channel to convey air through the catheter shaft 202 and to or from the balloon 204, so that the balloon 204 can selectively go from a deflated configuration to the inflated configuration and back again. The catheter shaft, and/or the balloon, can have a coating, such as those described herein, disposed thereon.

The present invention may be better understood with reference to the following examples. These examples are intended to be representative of specific embodiments of the invention, and are not intended as limiting the scope of the invention.

EXAMPLES

The following reagents, coating solutions, and substrates were used for the examples herein:

PA-BBA-AMPS-PEG

N-Acetylated poly[acrylamide$^{93.6\%}$-co-sodium-2-acrylamido-2-methylpropanesulfonate$^{4.9\%}$-co-N-(3-(4-benzoylbenzamido)propyl)methacrylamide$^{0.9\%}$]-co-methoxy poly(ethylene glycol)$_{1000}$ monomethacrylate$^{0.6\%}$ (percentages are mole percents) was obtained (PA-BBA-AMPS-PEG). This reagent can be prepared as described in U.S. Pat. Nos. 4,979,959; 5,263,992; and 5,512,329.

PA-AMPS-BBA-MA

Poly[acrylamide-co-sodium-2-acrylamido-2-methylpropanesulfonate-co-N-(3-(4-benzoylbenzamido)propyl)methacrylamide] was prepared according to the procedure described in U.S. Pat. Nos. 4,973,493, 5,002,582, and 5,263,992.

Photo-PVP

Polyvinylpyrrolidone having an average molecular weight of about 1,450 kDa with benzophenone photoreactive groups was prepared according to the methods described in U.S. Pat. No. 5,512,329.

BPP

The cross-linking agent sodium bis(4-benzoylphenyl) phosphate was prepared according to the methods described in U.S. Publ. Pat. App. No. 2012/0046384.

PVP-K90

Non-derivatized PVP (e.g., unmodified PVP) having an average molecular of 1,200 kDa was obtained from BASF.

DBDS

Disodium 4,5-bis[(4-benzoylbenzyl)oxy]-1,3-benzenedisulfonate (DBDS) was obtained. This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360).
TetraPhos: Tetra-Benzophenone Bisphosphonate

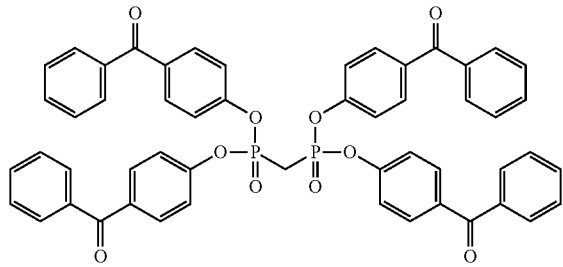 [SMILES: O=C(c1ccccc1)c1ccc(OP(=O)(CP(=O)(Oc2ccc(C(=O)c3ccccc3)cc2)Oc2ccc(C(=O)c3ccccc3)cc2)Oc2ccc(C(=O)c3ccccc3)cc2)cc1]

prepared according to the methods described in U.S. Publ. Pat. App. No. 2012/0046384.
TriPhos: Tri-Benzophenone Phosphate

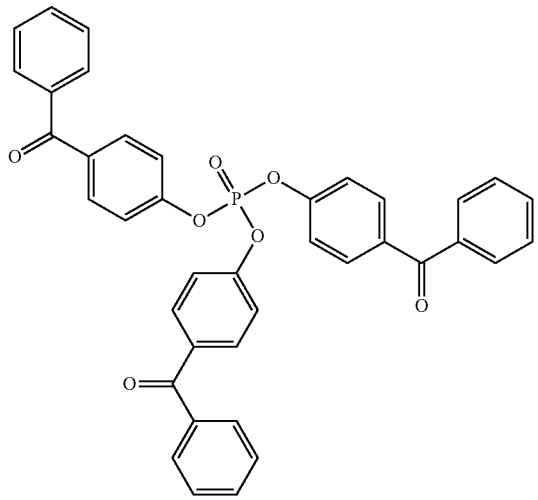 [SMILES: O=C(c1ccccc1)c1ccc(OP(=O)(Oc2ccc(C(=O)c3ccccc3)cc2)Oc2ccc(C(=O)c3ccccc3)cc2)cc1]

prepared according to the methods described in U.S. Publ. Pat. App. No. 2012/0046384.
DSE: Dibenzophenone Tetraisopropyldisiloxane

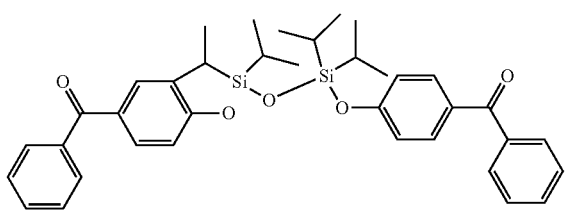

prepared according to the methods described in U.S. Publ. Pat. App. No. 2012/0046384.
Coating Solution A A coating solution was prepared by mixing together Photo-PVP at 13 g/L; PVP-K90 at 5 g/L; and sodium bis(4-benzoylphenyl) phosphate at 1 g/L in a solvent of 75% isopropyl alcohol and 25% water.
Coating Solution B A coating solution was prepared by mixing together Photo-PVP at 10.5 g/L; PA-BBA-AMPS-PEG at 10.5 g/L; sodium bis(4-benzoylphenyl) phosphate at 0.1 g/L in a solvent of 15% isopropyl alcohol and 85% water.
Coating Solution C A third coating solution was prepared by mixing together Photo-PVP at 13 g/L and sodium bis(4-benzoylphenyl) phosphate at 1 g/L in a solvent of 75% isopropyl alcohol and 25% water.
Coating Solution D A coating solution was prepared by mixing together Photo-PVP at 10.5 g/L; PA-AMPS-BBA-MA at 10.5 g/L; sodium bis(4-benzoylphenyl) phosphate at 0.1 g/L in a solvent of 15% isopropyl alcohol and 85% water.
Coating Solution E (w/PVP-K90)

A coating solution was prepared by mixing together Photo-PVP at 13 g/L; PVP-K90 at 5 g/L; and DBDS at 1 g/L in a solvent of 75% isopropyl alcohol and 25% water.
Coating Solution F A coating solution was prepared by mixing together Photo-PVP at 10.5 g/L; PA-BBA-AMPS-PEG at 10.5 g/L; DBDS at 0.1 g/L in a solvent of 15% isopropyl alcohol and 85% water.
Coating Solution G A coating solution was prepared by mixing together Photo-PVP at 16.36 g/L; and TetraPhos at 0.91 g/L in a solvent of 68% isopropyl alcohol and 32% acetone.
Coating Solution H A coating solution was prepared by mixing together Photo-PVP at 18 g/L; and TriPhos at 1 g/L in a solvent of 75% isopropyl alcohol and 25% acetone.
Coating Solution I A coating solution was prepared by mixing together Photo-PVP at 18 g/L; and DSE at 1 g/L in a solvent of 75% isopropyl alcohol and 25% water.
Coating Solution J A coating solution was prepared by mixing together Photo-PVP at 10 g/L; PA-BBA-AMPs-PEG at 10.5 g/L; and DSE at 0.1 g/L in a solvent of 25% isopropyl alcohol and 75% water.
Coating Solution K A coating solution was prepared by mixing together Photo-PVP at 18 g/L; and BPP at 1 g/L in a solvent of 75% isopropyl alcohol and 25% water.
Test Substrates Test substrates included Pebax rods (72D; 63D; and 35D-40% BASO$_4$) obtained from Medicine Lake Extrusion, Plymouth, Minn.; NYLON-12 rods obtained from Medicine Lake Extrusion, Plymouth, Minn.; PEEK rods obtained from Zeus, Orangeburg, S.C.; and high-density polyethylene (HDPE) rods available from Universal Plastics, Denver, Colo.
Friction (Lubricity) and Durability Testing The coated substrates of the examples were evaluated for lubricity/durability by friction measurements using a Vertical Pinch Method, as described in International Application Number WO 03/055611 with the following modifications. The coated substrates samples were inserted into the end of a rod holder, which was placed between the two jaws of a pinch tester and immersed in a cylinder of water or saline. The jaws of the pinch tester were closed as the sample was pulled in a vertical direction for 10 cm at a travel rate of 1 cm/sec and opened when the coated sample was returned to the original position. Unless otherwise specified herein, a 750 g force was applied as the coated substrates were pulled up through the pinched jaws. The pull force exerted on the substrate was then measured (grams). Pull force (g) is equal to the coefficient of friction (COF) multiplied by pinch force (g). The apparatus used for the vertical pinch test method is described in U.S. Pat. No. 7,348,055, the content of which is herein incorporated by reference.

Particulate Testing

Testing of the particulates generated in aqueous solution for the examples herein was performed according to the following procedure. As a derivative of the procedures described in ASTM F2394, substrates were passed through a tortuous path in an aqueous solution described as follows.

The distal portion of a 6 French guide catheter (Vista Brite Tip, Cordis) was cut off and discarded so that the catheter was 30 cm long. The guide catheter was inserted into the ASTM F2394-07 model. A hemostasis valve connector (Qosina) was attached to the guide catheter. The model was cleaned by flushing 120 ml Isoton (Becton, Dickinson, and Company) using a 60 ml syringe and discarding the flush. A base line flush with 60 ml Isoton was analyzed by light obscuration to determine background level of particulates. 60-cm rods (1 mm diameter) with 20 cm coated were hydrated in Isoton for ≥1 minute. The rods were inserted into the guide catheter and advanced until the distal portion of the rod exited the model. A 30 ml flush with Isoton was performed and collected in a glass beaker. The rod was removed and an additional 30 ml flush with Isoton was performed into the same glass beaker. The collected Isoton was immediately analyzed by light obscuration for particulates ≥10 and ≥25 microns. The model was cleaned with 120 ml Isoton and the next coated rod was tested.

Example 1: Formation of Lubricious Coating on 72D Pebax Rods

Coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source.

Next, coating solution B was applied to the first layer, also by dip coating at the same speed to form the second layer. The second layer was then air dried and UV cured using the same conditions as for the first layer.

Figure 3:
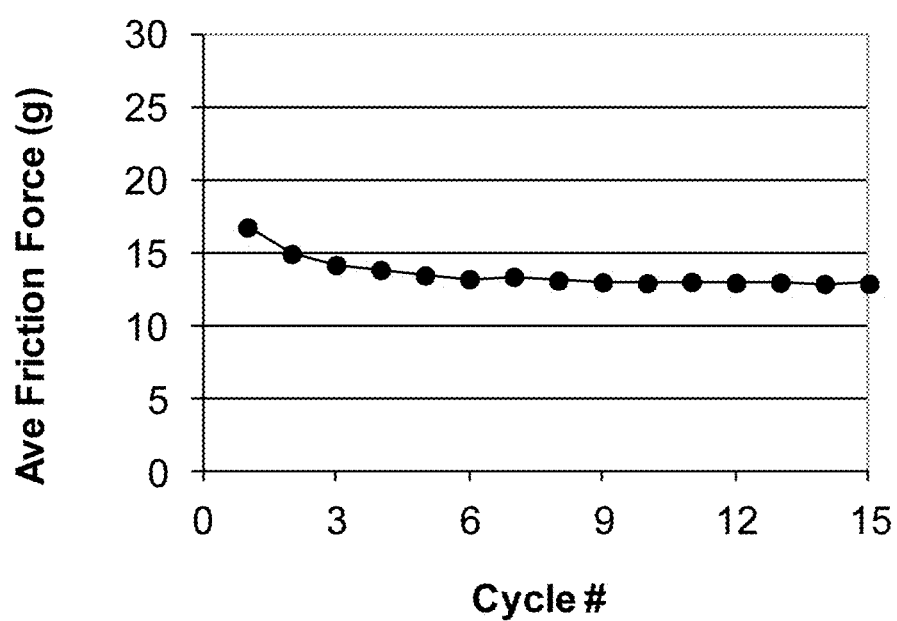
FIG. 3 is a graph showing the average measured frictional force in a vertical pinch test over a number of testing cycles.

The friction of the coating was then tested according to the testing procedure outlined above. The results are shown in FIG. 3.

Example 2: Effect of Variation of Polyacrylamide Containing Polymer in Second Layer Coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source.

Next, either coating solution B (n=4) or solution D (n=4) was applied to the first layer, also by dip coating at the same speed to form the second layer or top coat. The second layer was then air dried and UV cured using the same conditions as for the first layer.

Figure 4:
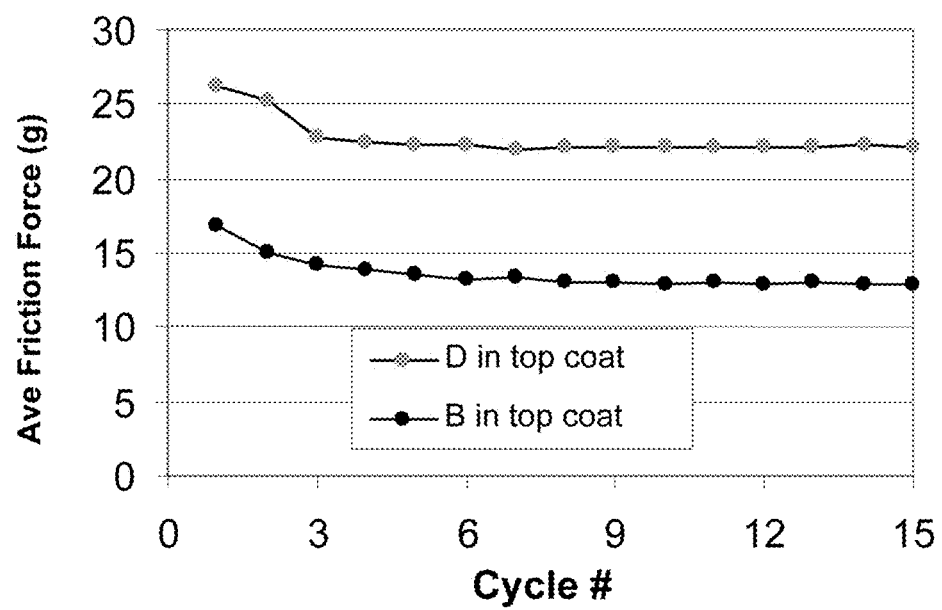
FIG. 4 is a graph showing the average measured frictional force in a vertical pinch test over a number of testing cycles.

The friction of the coating was then tested according to the testing procedure outlined above. The results are shown in FIG. 4.

Particulate generation testing was also performed. For an average of 3 rods, it was found that the PA-AMPS-BBA-MA group generated 4,447 (+/−567) particulates greater than 10 microns in size and the PA-BBA-AMPS-PEG group generated 4,140 (+/−725) particulates greater than 10 microns in size.

Example 3: Effect of Variation of Substrates on Lubricity and Durability

Coatings were deposited onto each of Pebax rods (72D; 63D; and 35D-40% $BASO_4$), NYLON-12 rods, PEEK rods, and HDPE rods.

Specifically, coating solution A was applied to each substrate using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source.

Next, coating solution B was applied to the first layer, also by dip coating at the same speed to form the second layer. The second layer was then air dried and UV cured using the same conditions as for the first layer.

Figure 5:
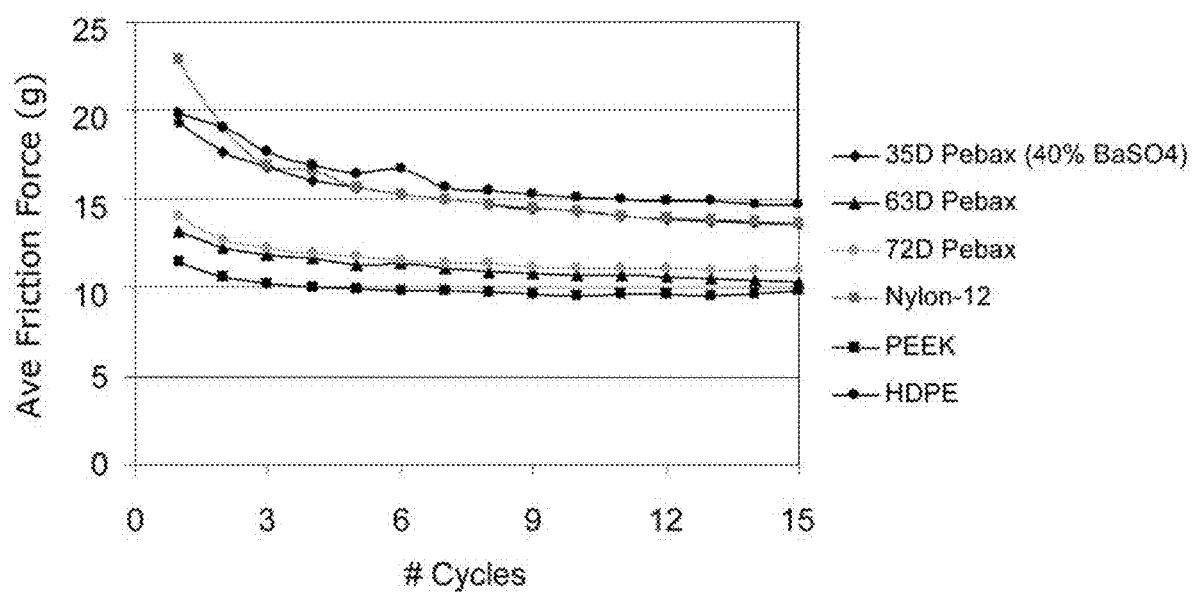
FIG. 5 is a graph showing the average measured frictional force in a vertical pinch test over a number of testing cycles.

The friction of the coating on each substrate was then tested according to the testing procedure outlined above. The results are shown in FIG. 5.

Example 4: Effect of Two-Layer Combinations on Lubricity and Durability

For a first set of rods (72D Pebax—n=7) coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source. Next, another layer of coating solution A was applied to the first layer, also by dip coating at the same speed to form the second layer. The second layer was then air dried and UV cured using the same conditions as for the first layer.

For a second set of rods (72D Pebax—n=4) coating solution B was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source. Next, another layer of coating solution B was applied to the first layer, also by dip coating at the same speed to form the second layer. The second layer was then air dried and UV cured using the same conditions as for the first layer.

For a third set of rods (72D Pebax—n=9) coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source. Next, a layer of coating solution B was applied to the first layer, also by dip coating at the same speed to form the second layer. The second layer was then air dried and UV cured using the same conditions as for the first layer.

Figure 6:
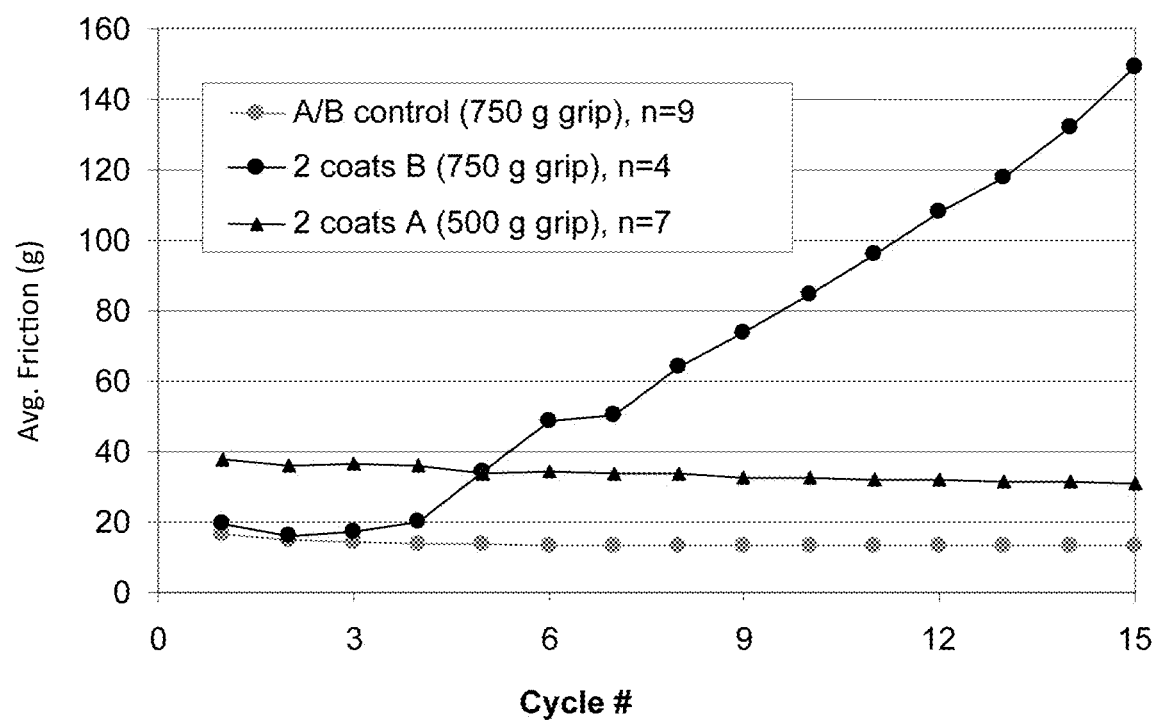
FIG. 6 is a graph showing the average measured frictional force in a vertical pinch test over a number of testing cycles.

The friction of the coating was then tested according to the testing procedure outlined above. The results are shown in FIG. 6. In addition, observations were made regarding the swelling behavior of the coatings. It was found that the first set of rods (including two "base" layers) exhibited the least amount of swelling. It was found that the second set of rods (including two "top" layers) exhibited the most swelling. It was found that the third set of rods (including a base layer and a top layer) exhibited an intermediate amount of swelling. Table 1 includes a summary of the coating thickness measurements and the calculated swelling ratio for each slide.

TABLE 1

Summary of the coating thickness measurements and the calculated swelling ratio for each slide.

| Sample ID: | Coating Thickness (μm) | | Swelling Ratio: |
| --- | --- | --- | --- |
| | Dry | Hydrated | (Wet/Dry) |
| A/A | | | |
| Slide 1 - meas. 1 | 1.07 | 2.78 | 2.6 |
| Slide 1 - meas. 2 | 1.14 | 3.02 | 2.6 |
| Slide 10 - meas. 1 | 0.43 | 1.42 | 3.3 |
| Slide 10- meas. 2 | 0.52 | 1.15 | 2.2 |
| Avg. Swell Ratio: | | | 2.7 ± 0.5 |
| B/B | | | |
| Slide 2 - meas. 1 | 0.57 | 3.48 | 6.1 |
| Slide 2 - meas. 2 | 0.73 | 4.42 | 6.1 |
| Slide 11 - meas. 1 | 0.41 | 2.41 | 5.9 |
| Slide 11 - meas. 2 | 0.35 | 2.36 | 6.7 |
| Avg. Swell Ratio: | | | 6.2 ± 0.3 |
| A/B | | | |
| Slide 3 - meas. 1 | 0.78 | 3.18 | 4.1 |
| Slide 3 - meas. 2 | 0.81 | 3.60 | 4.4 |
| Slide 12 - meas. 1 | 0.43 | 1.78 | 4.1 |
| Slide 12- meas. 2 | 0.42 | 1.90 | 4.5 |
| Avg. Swell Ratio: | | | 4.3 ± 0.2 |

Example 5: Effects of Cross-Linkers with Layers

For a first set ("In BC— base coat and TC—top coat") of rods coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source. Next, a layer of coating solution B was applied to the first layer, also by dip coating at the same speed to form the second layer. The second layer was then air dried and UV cured using the same conditions as for the first layer.

For a second set ("In TC Only") of rods a coating solution similar to A, except without sodium bis(4-benzoylphenyl) phosphate, was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source. Next, a layer of coating solution B was applied to the first layer, also by dip coating at the same speed to form the second layer. The second layer was then air-dried and UV cured using the same conditions as for the first layer.

For a third set ("In BC Only") of rods coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source. Next, a layer of a coating solution similar to B, except without sodium bis(4-benzoylphenyl) phosphate, was applied to the first layer, also by dip coating at the same speed to form the second layer. The second layer was then air dried and UV cured using the same conditions as for the first layer.

Figure 7:
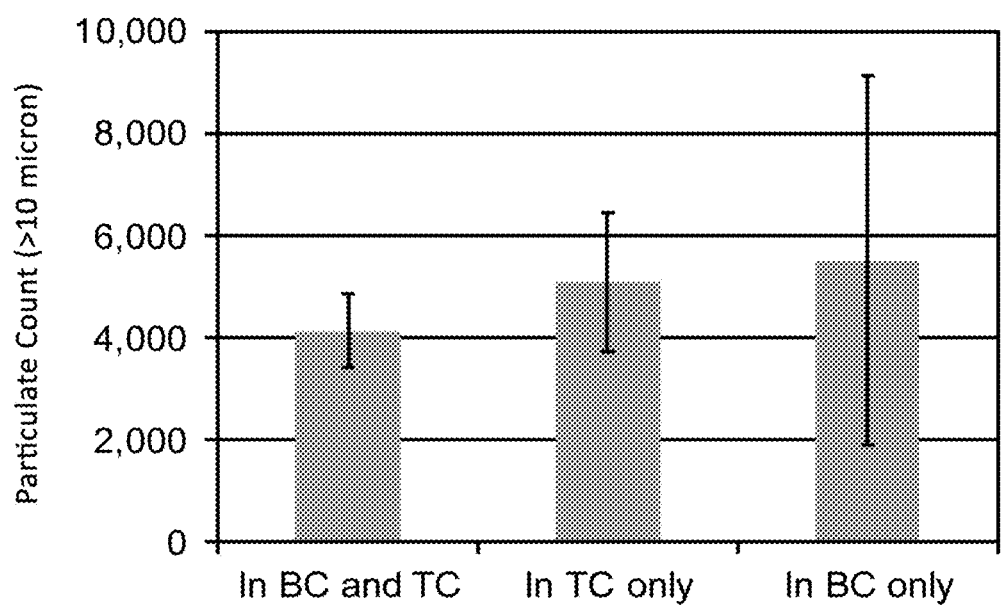
FIG. 7 is a graph showing measured particulates for various coatings.

The particulate generation of the coating was then tested according to the testing procedure outlined above. The results are shown in FIG. 7.

Example 6: Effects of Varying Amounts of Components in Second Layer

Coating solution A was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source.

Next, a layer of a coating solution was applied to the first layer, also by dip coating at the same speed to form the second layer. The different solutions used for the second coating layer were similar to coating solution B but the ratios of Photo-PVP: PA-BBA-AMPS-PEG varied. For the control, the ratio was 1:1 as in coating solution B. The other ratios were 1:2 and 2:1. In another coating solution, the photo-PVP was eliminated entirely. In yet another coating solution, the PA-BBA-AMPS-PEG (PBAP) was eliminated entirely. In all cases, the second layer was then air dried and UV cured using the same conditions as for the first layer.

Figure 8:
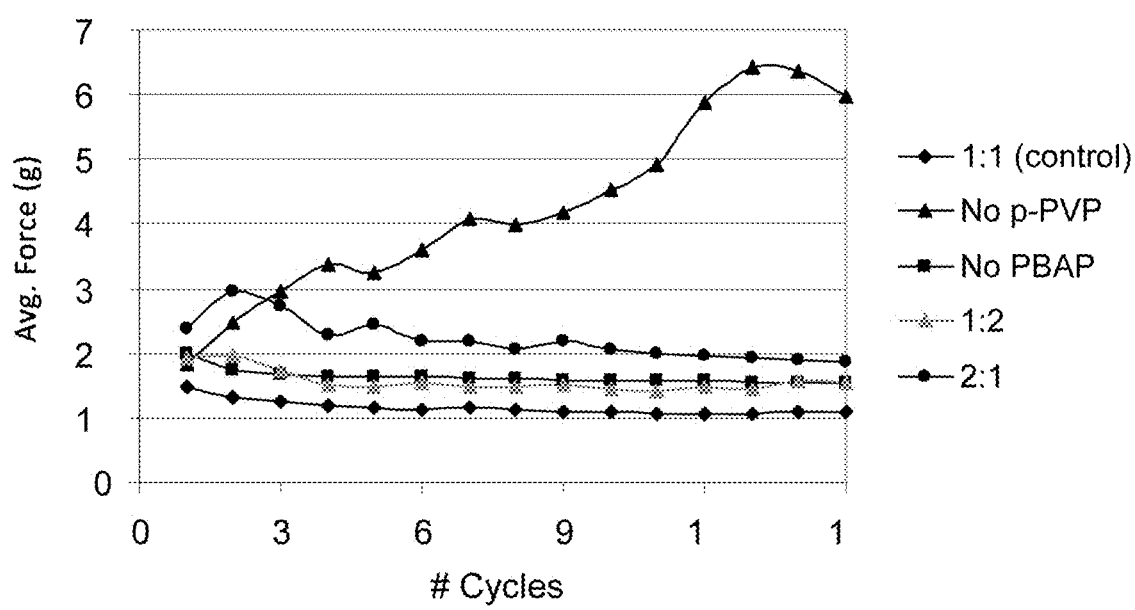
FIG. 8 is a graph showing the average measured frictional force in a vertical pinch test over a number of testing cycles.

The friction of the coating was then tested according to the testing procedure outlined above. The results are shown in FIG. 8.

Example 7: Effects of Variation of Viscosity and Dip Speed

Coating solution C was applied to a plurality of substrates (72D Pebax rods) using a dip coat method. Specifically, the substrate was immersed in the base coat coating solution with a dwell time of 5 seconds. The substrate was then extracted from the solution at a speed of 1.0 cm/s. The first layer was then UV cured without first drying. Specifically the coated substrate was rotated in front of a Dymax 2000-EC series UV flood lamp with a 400 Watt metal halide bulb for 30 seconds, approximately 20 cm from the light source.

Variations of coating solution B were prepared. One variation had a solids concentration sufficient to result in a coating solution with a viscosity of 20 cP. Another variation had a solids concentration sufficient to result in a coating solution with a viscosity of 13.8 cP. Yet another variation had a solids concentration sufficient to result in a coating solution with a viscosity of 8.91 cP. The substrate was then immersed in the coat coating solutions with a dwell time of 5 seconds and varying extraction speeds including 0.3; 0.5; 0.8; 1; 1.5; and 2 cm/s. The second layer was not allowed to dry, but immediately UV cured. Specifically the coated substrate was rotated in front of a Dymax 2000-EC series UV flood lamp with a 400 Watt metal halide bulb for 30 seconds, approximately 20 cm from the light source.

Figure 9:
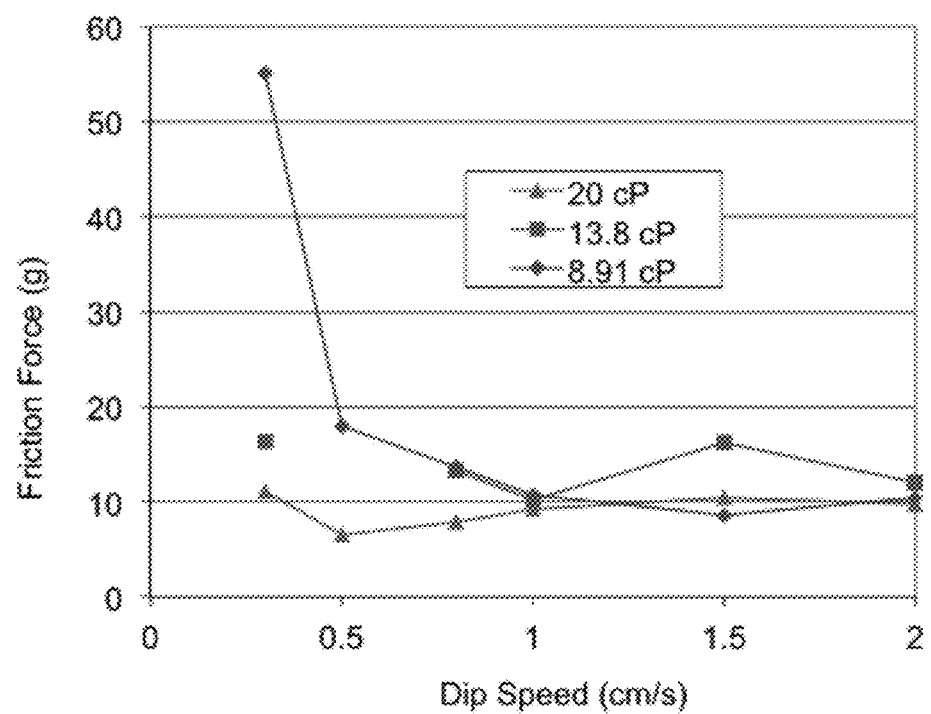
FIG. 9 is a graph showing measured frictional force in a vertical pinch test versus dip speed used for dip coating.

The friction of the coating was then tested according to the testing procedure outlined above. The results are shown in FIG. 9.

Figure 10:
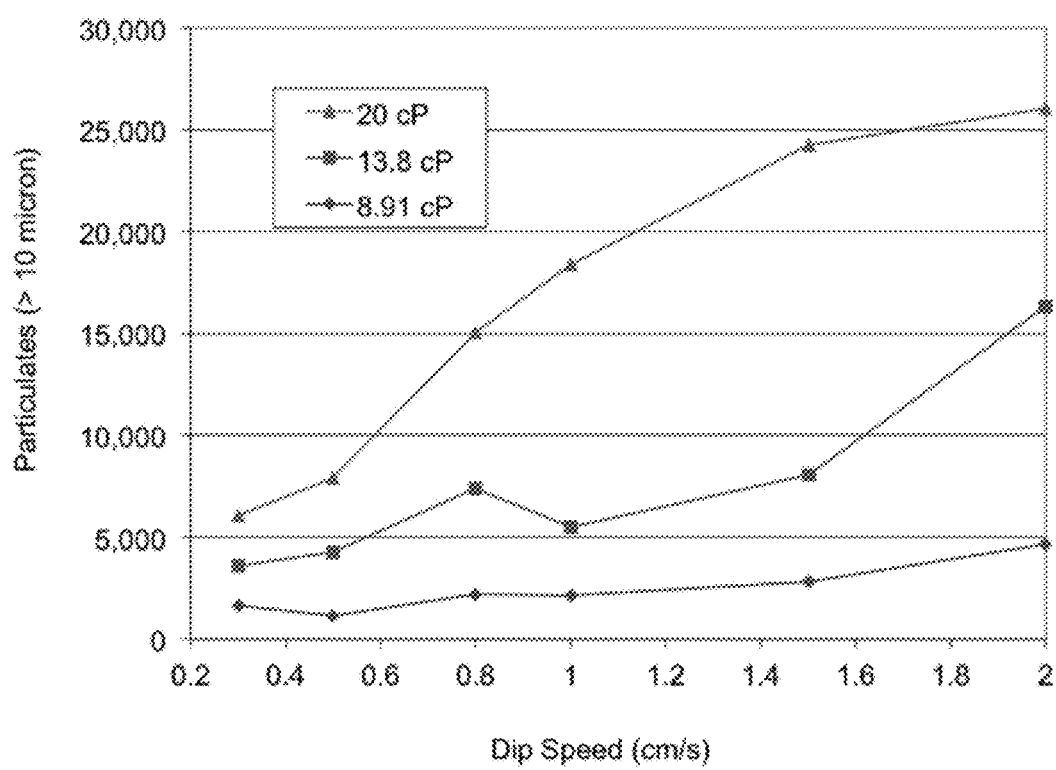
FIG. 10 is a graph showing measured particulates versus dip speed used for dip coating.

Particulates for the coatings were then tested according to the testing procedure outlined above. The results are shown in FIG. 10.

Example 8: Formation of Lubricious Coating on 72D Pebax Rods

Coating solution E was applied to the substrate (72D Pebax rods) using a dip coat method. Specifically, the substrate was immersed in the base coat coating solution with a dwell time of 5 seconds. The substrate was then extracted from the solution at a speed of 0.3 cm/s. The first layer was then air dried for at least 10 minutes. The first layer was then UV cured. Specifically the coated substrate was rotated in front of a Dymax 2000-EC series UV flood lamp with a 400 Watt metal halide bulb for 3 minutes, approximately 20 cm from the light source.

Next, coating solution F was applied to the first layer, also by dip coating at the same speed to form the second layer. The second layer was then air dried and UV cured using the same conditions as for the first layer.

Figure 11:
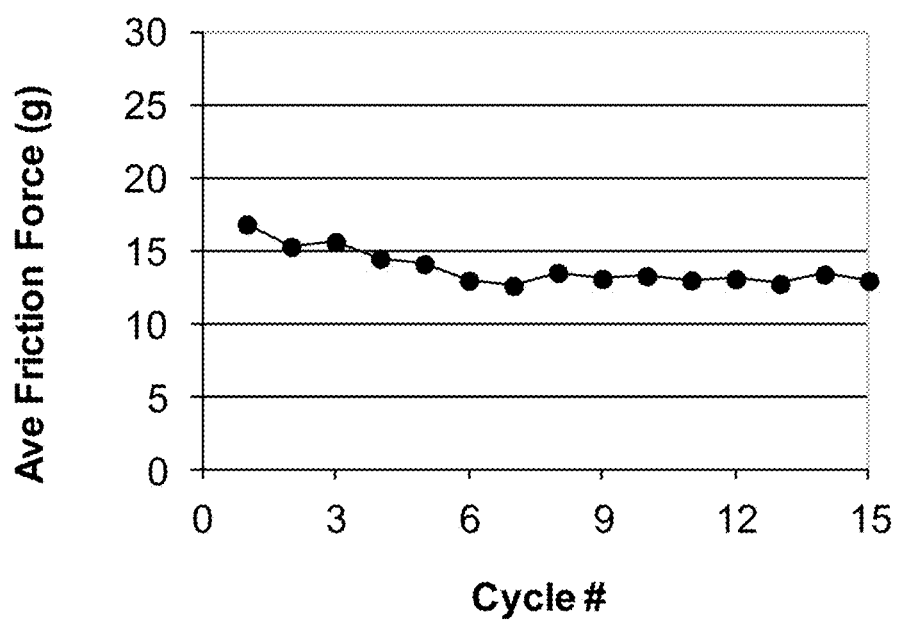
FIG. 11 is a graph showing the average measured frictional force in a vertical pinch test over a number of testing cycles.

The friction of the coating was then tested according to the testing procedure outlined above. The results are shown in FIG. 11.

Example 9: Effects of Different Cross-linkers in Base and/or Top Coats a) Coating solutions each of G, H, I or K were applied to four separate substrate material rods (72D Pebax rods) using a dip coat method and curing step as Example 1 (with the exception that coating K was dip coated at a rate of 1.5 cm/s). This coat served as the base coat for these four examples.

b) Coating solution B was applied to the first layer of G and H coated samples described in a) above using the same dip coat method and curing step as Example 1. This coat served as the top coat.

c) Coating solution J was applied to the first layer of I samples described in a) above using the same dip coat method and curing step as Example 1. This coat served as the top coat.

d) Coating solution B was applied to the first layer of K samples described in a) above using the same dip coat method and curing step as Example 1. This coat served as the top coat.

Figure 12:
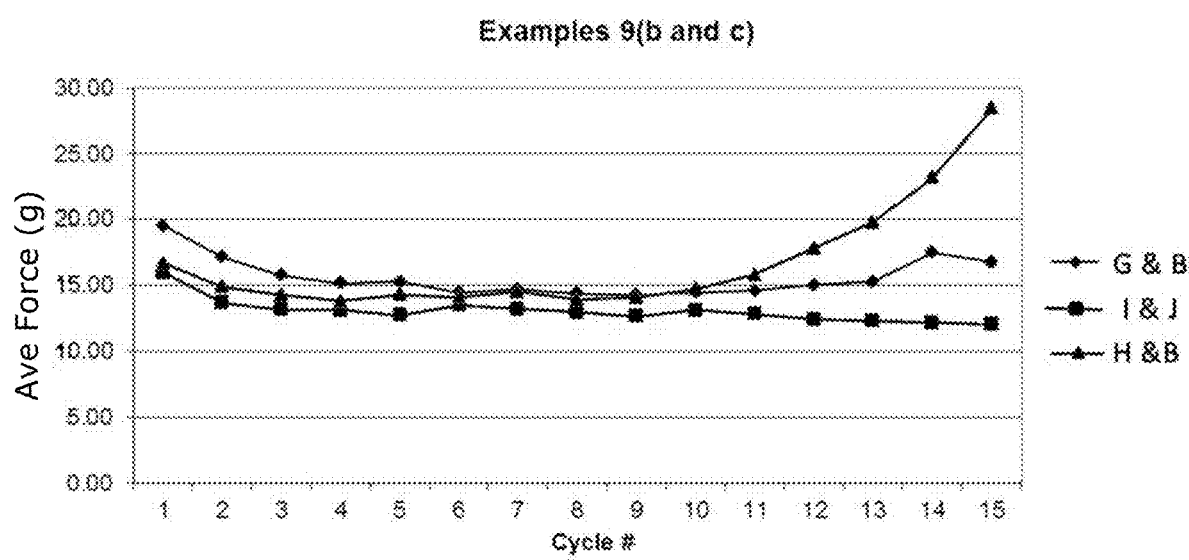
FIG. 12 is a graph showing the average measured frictional force in a vertical pinch test over a number of testing cycles.
Figure 13:
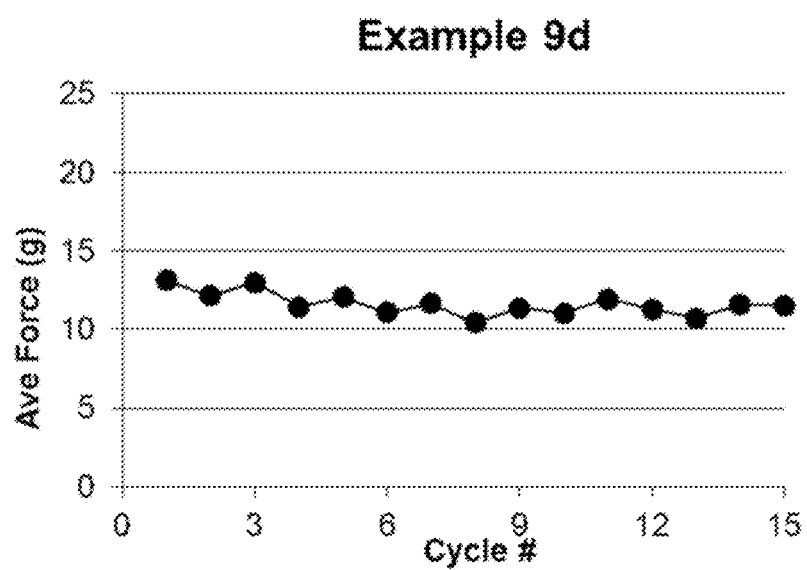
FIG. 13 is a graph showing the average measured frictional force in a vertical pinch test over a number of testing cycles.

The friction (FIGS. 12 and 13) and particulate testing (Table 2) was then performed according to the testing procedures described above.

TABLE 2

| Example | No. Particulates >10 μm |
|---|---|
| 9b - H&B | 12,247 |
| 9b - G&B | 11,932 |
| 9c | 19,698 |
| 9d | 6,567 |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention has been described with reference to various specific and preferred embodiments and techniques. However, it should be understood that many variations and modifications may be made while remaining within the spirit and scope of the invention.

The invention claimed is:

1. A coating for a medical device comprising:
   a first layer comprising
      a first polymer composition comprising a polyvinylpyrrolidone derivatized with a photoreactive group; and
      a first ionic cross-linking agent comprising at least two photoreactive groups;
   a second layer disposed on the first layer, the second layer distinct from the first layer, comprising
      a second polymer composition comprising a polyvinylpyrrolidone derivatized with a photoreactive group, wherein the first polyvinylpyrrolidone derivatized with a photoreactive group and the second polyvinylpyrrolidone derivatized with a photoreactive group are the same; and
      a second ionic cross-linking agent comprising at least two photoreactive groups;

wherein the first polymer composition of the first layer and the second polymer composition of the second layer are the same;

wherein the first ionic cross-linking agent is present in the first layer in a first concentration and the second ionic cross-linking agent is present in the second layer in a second concentration;

wherein the first concentration of the first ionic cross-linking agent present in the first layer is higher than the second concentration of the second ionic cross-linking agent present in the second layer such that the first concentration of the first ionic cross-linking agent comprises a higher concentration of photoreactive groups than the second concentration of the second ionic cross-linking agent in the second layer;

wherein the first ionic cross-linking agent and the second ionic cross-linking agent confer an ionic charge to both the first layer and the second layer, and wherein the ionic charge of the first and second layer are both anionic or both cationic; and wherein the coating releases less than 10,000 particles greater than 10 microns in size when exposed to an aqueous environment.

2. The coating of claim 1, wherein the first ionic cross-linking agent is different from the second ionic cross-linking agent.

3. The coating of claim 1, the first layer and the second layer further comprising a polymer comprising polyacrylamide, 2-acrylamido-2-methylpropanesulfonate (AMPS), and polyethyleneglycol subunits.

4. The coating of claim 1, the first layer and the second layer further comprising a polymer comprising N-Acetylated poly[acrylamide-co-sodium-2-acrylamido-2-methylpropanesulfonate-co-N-(3-(4-benzoylbenzamido)propyl) methacrylamide]-co-methoxy poly(ethylene glycol) monomethacrylate.

5. The coating of claim 1, wherein the ratio of the first polyvinylpyrrolidone derivatized with a photo reactive group in the first layer to the first ionic cross-linking agent comprising at least two photoreactive groups is from about 8:1 to about 16:1 (wt./wt.).

6. The coating of claim 1, wherein the ratio of the first polyvinylpyrrolidone derivatized with a photo reactive group in the first layer to the first ionic cross-linking agent comprising at least two photoreactive groups is about 13:1 (wt./wt.).

7. The coating of claim 1, at least one of the first and second ionic cross-linking agents comprising a linking agent having formula Photo$^1$-LG-Photo$^2$, wherein Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

8. The coating of claim 1, at least one of the first and second ionic cross-linking agents comprising a linking agent having a formula selected from:

(a)

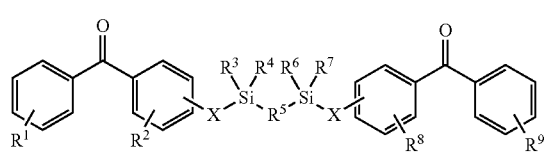

wherein R1, R2, R8 and R9 are H; R3, R4, R6 and R7 are —CH3; R5 is —C$_2$H$_4$—; and each X is O; and (b)

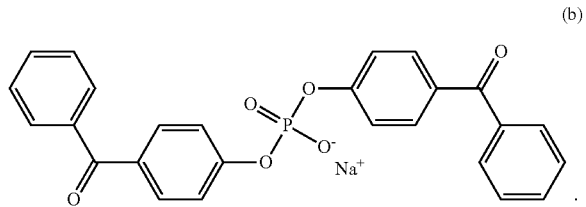 [SMILES: O=C(c1ccccc1)c1ccc(OP(=O)([O-])Oc2ccc(C(=O)c3ccccc3)cc2)cc1 ; [Na+]]

9. The coating of claim 1, at least one of the first and second ionic cross-linking agents comprising sodium bis(4-benzoylphenyl) phosphate (BPP).

10. The coating of claim 1, at least one of the first and second ionic cross-linking agents comprising ethylenebis (4-benzoylbenzyldimethylammonium) dibromide.

11. The coating of claim 1, the first layer further comprising non-derivatized polyvinylpyrrolidone.

12. The coating of claim 11, wherein the ratio of the first polyvinylpyrrolidone derivatized with a photoreactive group in the first layer to non-derivatized polyvinylpyrrolidone in the first layer to the first ionic cross-linking agent comprising at least two photoreactive groups is from about 13:0.1:1 to 13:8:1.

13. The coating of claim 1, the coating exhibiting a lubricity when wetted of between 0 and 30 grams of force.

14. The coating of claim 1, the coating exhibiting a lubricity when wetted of between 0 and 30 grams of force for at least 10 consecutive testing cycles.

15. The coating of claim 1, the coating exhibiting a durability of lubricity such there is less than a 30 percent increase in measured friction between the average of cycles 1-5 of testing and cycles 10-15 of testing.

16. The coating of claim 1, wherein the thickness of the first layer and second layer combined is between about 100 and 3000 nm when dry.

17. The coating of claim 1, wherein the photoreactive groups are benzophenone.

18. A coating for a medical device comprising:
a first layer comprising
a first polymer composition comprising a polyvinylpyrrolidone derivatized with a photoreactive group; and
a first ionic cross-linking agent comprising at least two photoreactive groups; and
a second layer disposed on the first layer, the second layer distinct from the first layer, comprising
a second polymer composition comprising a polyvinylpyrrolidone derivatized with a photoreactive group, wherein the first polyvinylpyrrolidone derivatized with a photoreactive group and the second polyvinylpyrrolidone derivatized with a photoreactive group are the same; and
a second ionic cross-linking agent comprising at least two photoreactive groups;
wherein the first polymer composition of the first layer and the second polymer composition of the second layer are the same;
wherein the first ionic cross-linking agent is present in the first layer in a first concentration and the second ionic cross-linking agent is present in the second layer in a second concentration;
wherein the first concentration of the first ionic cross-linking agent present in the first layer is higher than the second concentration of the second ionic cross-linking agent present in the second layer such that the first concentration of the first ionic cross-linking agent comprises a higher concentration of photoreactive groups than the second concentration of the second ionic cross-linking agent in the second layer;

wherein the first ionic cross-linking agent and the second ionic cross-linking agent confer an ionic charge to both the first layer and the second layer, and wherein the ionic charge of the first and second layer are both anionic or both cationic; and wherein the coating releases less than 1,592 particles greater than 10 microns in size per square centimeter of coating surface area when exposed to an aqueous environment.

19. The coating of claim 1, wherein the first ionic cross linking agent and the second ionic cross-linking agent are both cationic.

20. The coating of claim 1, wherein the first ionic cross linking agent and the second ionic cross-linking agent are both anionic.

* * * * *